(12) United States Patent
Sakamoto et al.

(10) Patent No.: US 10,661,101 B2
(45) Date of Patent: May 26, 2020

(54) DOSE DISTRIBUTION CALCULATION DEVICE, PARTICLE BEAM THERAPY SYSTEM, AND DOSE DISTRIBUTION CALCULATION METHOD

(71) Applicant: Hitachi, Ltd., Tokyo (JP)

(72) Inventors: Yusuke Sakamoto, Tokyo (JP); Hiroshi Nishizawa, Tokyo (JP); Masateru Hayashi, Tokyo (JP); Tetsushi Azuma, Tokyo (JP); Kazuo Yamamoto, Tokyo (JP); Yukiko Hirano, Tokyo (JP); Natsuko Maeda, Tokyo (JP); Eri Hattori, Tokyo (JP); Taizo Honda, Tokyo (JP); Yasuto Kishii, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 157 days.

(21) Appl. No.: 15/740,210

(22) PCT Filed: Jul. 1, 2015

(86) PCT No.: PCT/JP2015/069001
§ 371 (c)(1),
(2) Date: Dec. 27, 2017

(87) PCT Pub. No.: WO2017/002231
PCT Pub. Date: Jan. 5, 2017

(65) Prior Publication Data
US 2018/0311513 A1  Nov. 1, 2018

(51) Int. Cl.
*A61N 5/10* (2006.01)

(52) U.S. Cl.
CPC ......... *A61N 5/1065* (2013.01); *A61N 5/1031* (2013.01); *A61N 5/1071* (2013.01);
(Continued)

(58) Field of Classification Search
None
See application file for complete search history.

(56) References Cited

U.S. PATENT DOCUMENTS

2004/0213381 A1  10/2004  Harada
2006/0203964 A1   9/2006  Nyholm et al.
(Continued)

FOREIGN PATENT DOCUMENTS

EP       2186542 A1 *  5/2010
JP     2004-321408 A   11/2004
(Continued)

OTHER PUBLICATIONS

International Search Report (PCT/ISA/210) dated Oct. 6, 2015, by the Japanese Patent Office as the International Searching Authority for International Application No. PCT/JP2015/069001.
T. Inaniwa et al., "Development of treatment planning for scanning irradiation at HIMAC", Nuclear Instruments and Methods in Physics Research B 266, 2008, pp. 2194-2198.
Standardization of the absorbed dose measurement in IMRT, Research Project Supported in FY2008—FY2009, Japan Society of Medical Physics, 7 pages.

*Primary Examiner* — Andrew Smyth
(74) *Attorney, Agent, or Firm* — Mattingly & Malur, PC

(57) ABSTRACT

A dose distribution calculation device of the invention is characterized by including: a beam information storing unit (a measured energy storing unit, a measured electric-charge storing unit, a measured beam-central axis storing unit), in which, when particle beam information of a particle beam generated by a particle beam therapy system is measured by a measuring device in confirmative radiation in which the particle beam is radiated to a phantom as a substitute for a treatment target, the thus-measured particle beam information is stored; and a total dose calculation unit for calculating a radiation dose distribution (a total dose distribution) on the basis of the measured particle beam information (a measured energy, a measured beam quantity (a measured number of electric charges), a measured position of beam central axis).

20 Claims, 6 Drawing Sheets

(52) U.S. Cl.
CPC .......... *A61N 5/1075* (2013.01); *A61N 5/1043* (2013.01); *A61N 5/1077* (2013.01); *A61N 2005/1076* (2013.01); *A61N 2005/1087* (2013.01)

(56) References Cited

U.S. PATENT DOCUMENTS

| | | |
|---|---|---|
| 2010/0177872 A1 | 7/2010 | Müller et al. |
| 2010/0215147 A1 | 8/2010 | Müller et al. |
| 2012/0161030 A1 | 6/2012 | Iwata et al. |
| 2012/0232324 A1 | 9/2012 | Brusasco et al. |
| 2012/0305796 A1 | 12/2012 | Iseki et al. |
| 2015/0071408 A1 | 3/2015 | Ebstein |
| 2015/0251021 A1* | 9/2015 | Boisseau .............. A61N 5/1075 250/252.1 |
| 2016/0325116 A1* | 11/2016 | Sakamoto ............ A61N 5/1043 |

FOREIGN PATENT DOCUMENTS

| | | | |
|---|---|---|---|
| JP | 2007141754 A | * | 6/2007 |
| JP | 2010-508107 A | | 3/2010 |
| JP | 4936723 B2 | | 5/2012 |
| JP | 5417644 B2 | | 2/2014 |
| JP | 2014-54438 A | | 3/2014 |
| JP | 2014054438 A | * | 3/2014 |
| JP | 5555826 B2 | | 7/2014 |
| JP | 5571070 B2 | | 8/2014 |
| WO | WO 2012/086062 A1 | | 6/2012 |
| WO | WO 2016088155 A1 | * | 6/2016 |

* cited by examiner

| Time Point | t1 | t2 | t3 | ... | tn |
|---|---|---|---|---|---|
| Measured Number of Electric Charges | Q(t1) | Q(t2) | Q(t3) | ... | Q(tn) |
| Measured Energy | E(t1) | E(t2) | E(t3) | ... | E(tn) |
| Measured Position of Beam Central Axis | Px(t1) Py(t1) | Px(t2) Py(t2) | Px(t3) Py(t3) | ... | Px(tn) Py(tn) |

35

DOSE DISTRIBUTION CALCULATION DEVICE, PARTICLE BEAM THERAPY SYSTEM, AND DOSE DISTRIBUTION CALCULATION METHOD

TECHNICAL FIELD

The present invention relates to a particle beam therapy system for radiating a beam of particles such as protons, carbon ions or the like (particle beam) to a diseased site such as a tumor or the like to thereby perform its treatment, said particle beam therapy system being used for radiating the particle beam with a specified dose in conformity with a three-dimensional shape of the diseased site.

BACKGROUND ART

A particle therapy is a cancer treatment method which comprises accelerating charged particles such as protons, carbon ions or the like up to about a several hundreds mega-electron volt by use of an instrument such as an accelerator or the like, followed by radiating them to a patient to thereby impart a dose to a tumor in his/her body. At this time, for the tumor, it is important to form a dose distribution that is as close as possible to a dose distribution ordered by a doctor, namely, a target distribution. In many cases, the target distribution is such a distribution in which the dose in the tumor is as uniform as possible and the dose outside the tumor is as lower as possible than that in the tumor.

In general, when the particle beam accelerated by an accelerator is radiated to an object (examples of which include a human body), the three-dimensional dose distribution in the object has a feature of having a maximum dose peak at one certain point. The maximum dose peak is referred to as Bragg peak. In addition, when the distribution has the maximum dose peak at one point in a three-dimensional space, the position of such a peak is defined as "irradiation position" of that particle beam. In order to three-dimensionally form the target distribution using the particle beam with such a peak structure described above, some kind of ingenuity is required.

As one method for forming the target distribution, there is a scanning irradiation method. In order to employ this method, firstly, such a feature is used that arbitrarily deflects, using electromagnets, etc., the particle beam in two directions perpendicular to a Z-direction that is a traveling direction of the particle beam, namely, X and Y-directions. Further, such a feature is required that adjusts the energy of the particles to thereby arbitrarily adjust in the Z-direction, the position at which the Bragg peak is formed. Generally, a particle beam generation-transportation apparatus that performs transportation and interruption of the particle beam is provided with an accelerator for accelerating the particle beam, and the accelerator also has an energy adjusting function. Then, upon setting a plurality of irradiation positions (referred to also as spots) in the tumor, the particle beam is radiated using the above two features, sequentially to the respective irradiation positions. The balance among the doses to be individually imparted to the respective irradiation positions has been adjusted and determined beforehand, so that the target distribution is formed as the result of totaling the respective dose distributions applied to the respective irradiation positions.

According to the scanning irradiation method, because various uncertain factors exist in actual irradiation, there is a possibility that, although the target distribution must be obtained on a calculation basis, the dose distribution actually obtained is not matched to the target distribution. The uncertain factors includes, for example, a temporal change in the particle beam quantity, a temporal change or a hysteresis in the magnetic field of a scanning electromagnet, a sensitivity variation of a dose monitor, a signal delay and/or a noise of a control device, and the like. It is thought that, due to influence by them, an actual dose distribution possibly becomes different from the calculated values.

In order to eliminate the uncertainties, such an operation is generally performed in which, after the preparation of plan for a particle beam therapy but before the radiation of the beam to a patient, beam radiation is executed to a phantom (a substitute for the patient) in a condition as equal as possible to that of the plan, so that a value of absolute dose (absolute dose value) and a dose distribution therein are measured and confirmed whether they are accommodated to the plan. This operation is referred to as a patient QA (Quality Assurance). As the phantom, water filled in a water tank is generally used in many cases, so that the dose is measured using a dose measuring device placed in the water. In view of the purpose of the patient QA, it is desired to confirm not only the absolute dose value at the center of the tumor but also the dose distribution therearound, and therefore, it is desired to measure the doses at multiple measuring points.

CITATION LIST

Patent Document

Patent Document 1: Japanese Patent No. 5555826 (Paragraph 0015, Paragraphs 0035 to 0040; FIG. 3)
Patent Document 2: Japanese Patent No. 4936723 (Paragraphs 0008 to 0015)
Non-Patent Document 1: T. Inaniwa, et al., "Development of treatment planning for scanning irradiation at HIMAC", Nuclear Instruments and Methods in Physics Research B 266(2008)2194-2198
Non-Patent Document 2: "Standardization of the absorbed dose measurement in IMRT", Research Project Supported in FY2008-FY2009, Japan Society of Medical Physics

SUMMARY OF THE INVENTION

Problems to be Solved by the Invention

At the time of measuring the dose distribution in particle-beam scanning irradiation, when a dosimeter using a usual ionization chamber is employed, the dose can be measured only at one point per one scanning irradiation. Accordingly, when the doses at multiple points are to be measured, the scanning irradiation has to be executed plural number of times, the number of which is the same as the number of the measuring points, and this takes time. Meanwhile, in a conventional particle beam therapy facility, an upper limit of beam radiation quantity allowed to be radiated per one week is specified. Because the patient QA is required to be executed for every patient, there is a problem that, when the time and the number of irradiation times taken for the patient QA increase, the number of patients who can be accepted by the therapy facility, namely who can be treated, decreases.

As a simple method for solving the above problem, a method of measuring the doses at multipoints at one time is conceivable. For example, using a radiosensitive film makes it possible to measure a dose distribution in a two-dimensional plane at one time. This method, however, involves problems of inter-lot variation in the film production, radiation-quality dependence on the dose and the sensitivity of the film, and the like, so that its measurement accuracy is generally lower than that of the ionization chamber. Further, as for another method of measuring the doses at multipoints at one time, many small ionization chambers may be arranged. This method, however, involves difficulties in getting machining accuracy, wiring and the like, so that it is difficult to make the arrangement interval of the ionization chambers less than about 1 cm. In addition, there is a possibility that scattered parts of the particle beam after hitting an electrode of the ionization chamber makes an effect on the measured value of the other ionization chamber, so that the measurement accuracy is thought to be lowered likewise.

In Patent Document 1, a method and a device for performing patient-specific IMRT verification are described. The IMRT verification method in Patent Document 1 is a method in which a distribution of radiated photon fluence (the number of particles passing a sphere of unit cross-sectional area) corresponding the beam, is re-established based on responses of a two-dimensional detector (two-dimensional dose detector), and a three-dimensional dose distribution is calculated based on the re-established distribution of the radiated photon fluence. According to the IMRT verification method in Patent Document 1, the three-dimensional dose distribution in a target three-dimensional image is achieved only from two-dimensionally measured information, so that it is a method that can accomplish a fast patient QA. However, according to the IMRT verification method in Patent Document 1, when high accuracy and high positional resolution are required for three-dimensional dose calculation, in association therewith, accuracy and positional resolution for two-dimensional detection by the two-dimensional detector have to be high, so that a concern may arise that it becomes difficult to develop and manufacture such a two-dimensional detector, and to use it for that method.

In Patent Document 2, a method and a device for performing calculation of radiation dose distribution for a radiation therapy system, using a limited amount of data, are described. In Patent Document 2, a beam quality index that is representative of a radiation beam is determined, and a radiation dose distribution is calculated using parameterized dose deposition kernels based on the beam quality index. In the patient QA according to this method, it is possible to eliminate static uncertainties in dose calculation due to variation between devices or characteristics thereof, a shape of the patient's tumor, a shape of the radiation field, and the like. However, in the patient QA according to the method in Patent Document 2, it is difficult to eliminate dynamic uncertainties due to, for example, a rapid temporal change in the beam quantity, a delay or noise in a control circuit for changing a value of the current for the scanning electromagnet, and the like.

Accordingly, an object of the present invention is with respect to a patient QA for a particle-beam scanning treatment, and to accomplish a patient QA which requires no dose detector having high positional resolution and in which both the static and dynamic uncertainties are eliminated.

Means for Solving the Problems

The dose distribution calculation device of this invention is a dose distribution calculation device for calculating, when a particle beam therapy system performs a particle beam therapy by scanning using a scanning device a particle beam on a treatment target, a radiation dose distribution to be applied by the particle beam therapy system to the treatment target, said dose distribution calculation device characterized by comprising: a beam information storing unit in which, when particle beam information of the particle beam generated by the particle beam therapy system is measured by a measuring device in confirmative radiation in which the particle beam is radiated to a phantom as a substitute for the treatment target, the thus-measured particle beam information is stored; and a total dose calculation unit for calculating the radiation dose distribution on the basis of the measured particle beam information.

Effect of the Invention

According to the dose distribution calculation device of the invention, the radiation dose distribution is calculated based on the measured particle beam information, so that it is possible to accomplish a patient QA which requires no dose detector having high positional resolution and requires no measurement of doses at many points in the phantom, and in which both the static and dynamic uncertainties are eliminated.

MODES FOR CARRYING OUT THE INVENTION

Embodiment 1

Figure 1:
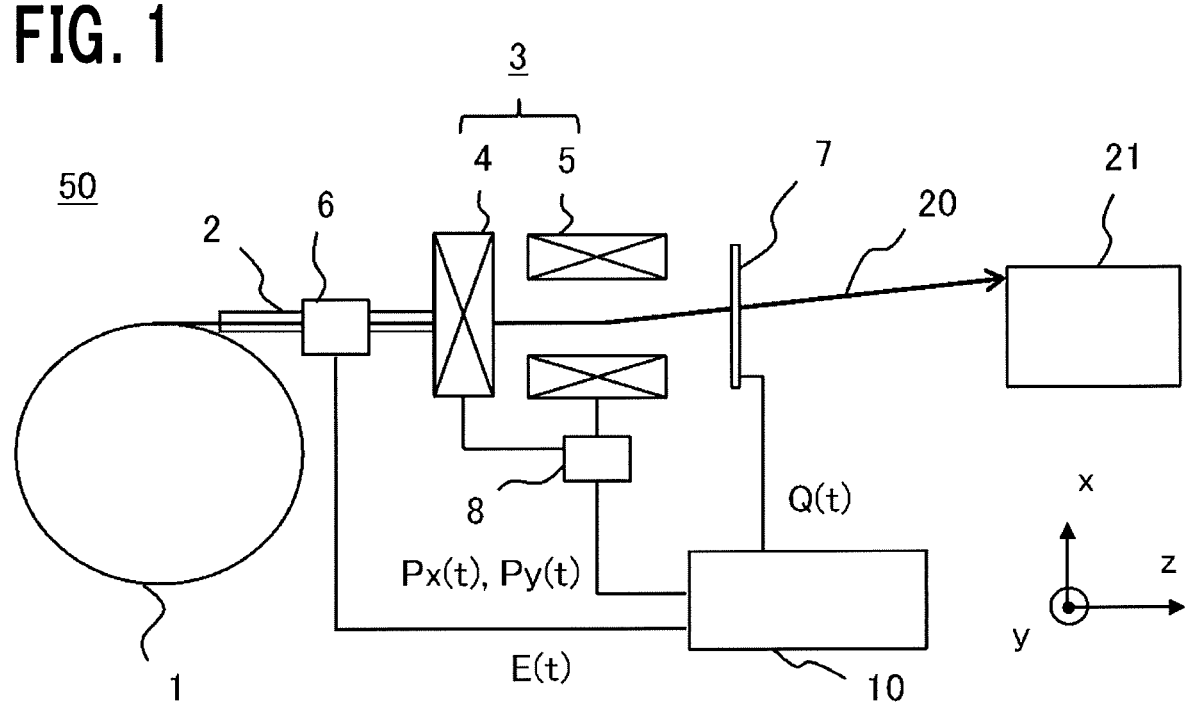
FIG. 1 is a schematic configuration diagram of a particle beam irradiation apparatus at the time a patient QA is executed, according to Embodiment 1 of the invention.
Figure 2:
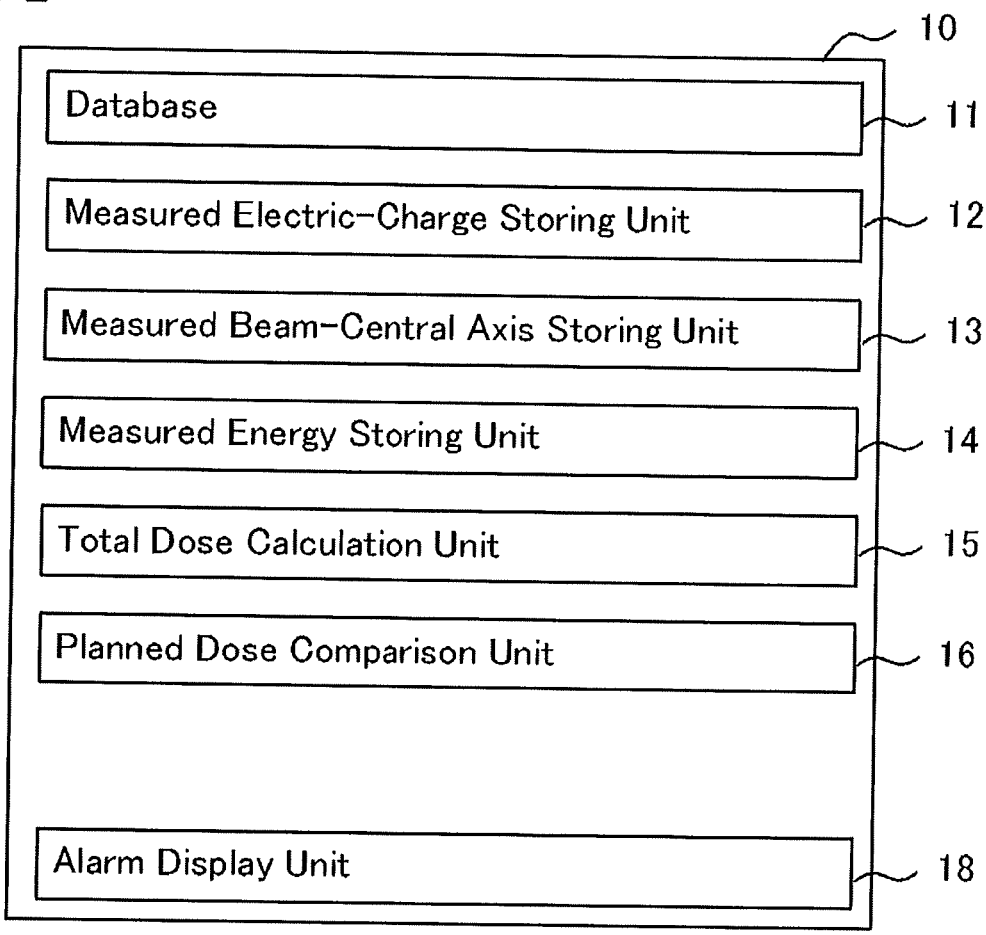
FIG. 2 is a diagram showing a configuration of a dose distribution calculation device in FIG. 1.
Figure 3:
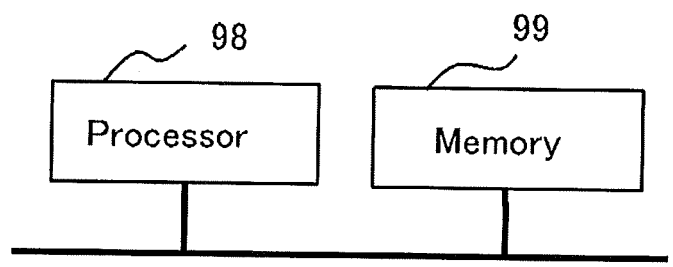
FIG. 3 is a diagram showing a hardware configuration by which functional blocks in FIG. 2 are implemented.
Figures 4, 5:
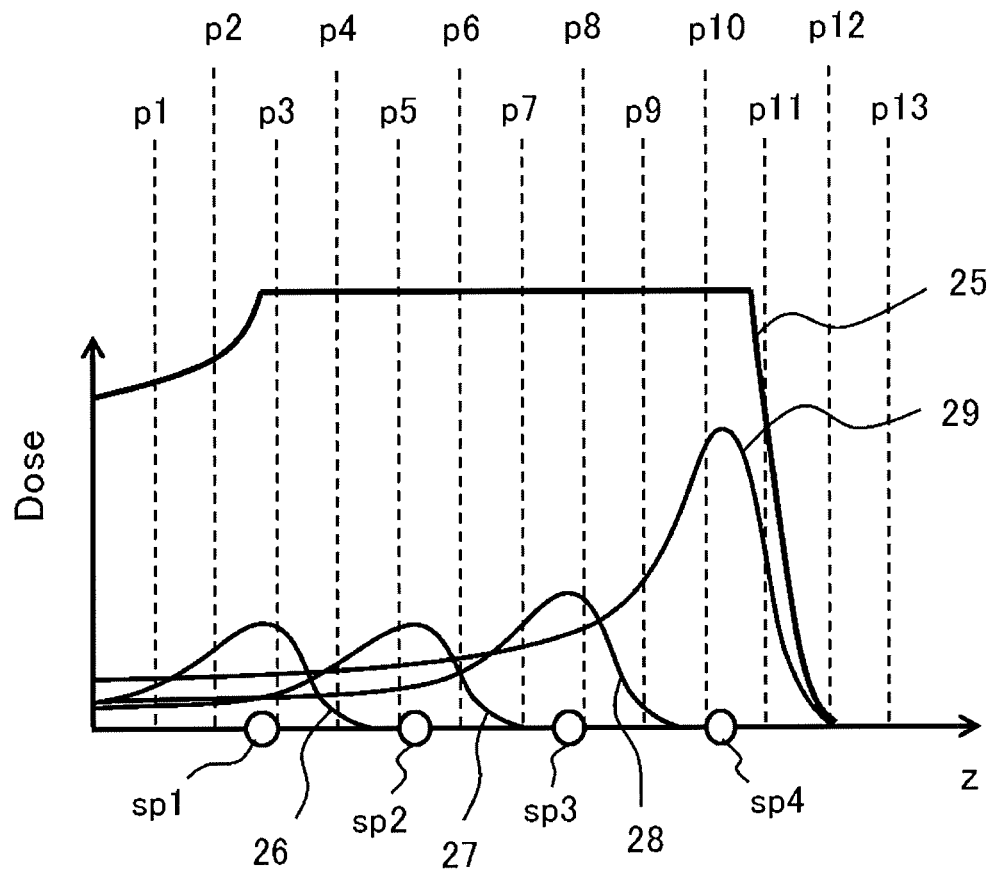
FIG. 4 is a diagram showing an example of a structure of data to be inputted to the dose distribution calculation device in FIG. 1.
FIG. 5 is a diagram illustrating an example of a total dose distribution and dose evaluation points in a patient QA, according to Embodiment 1 of the invention.
Figure 6:
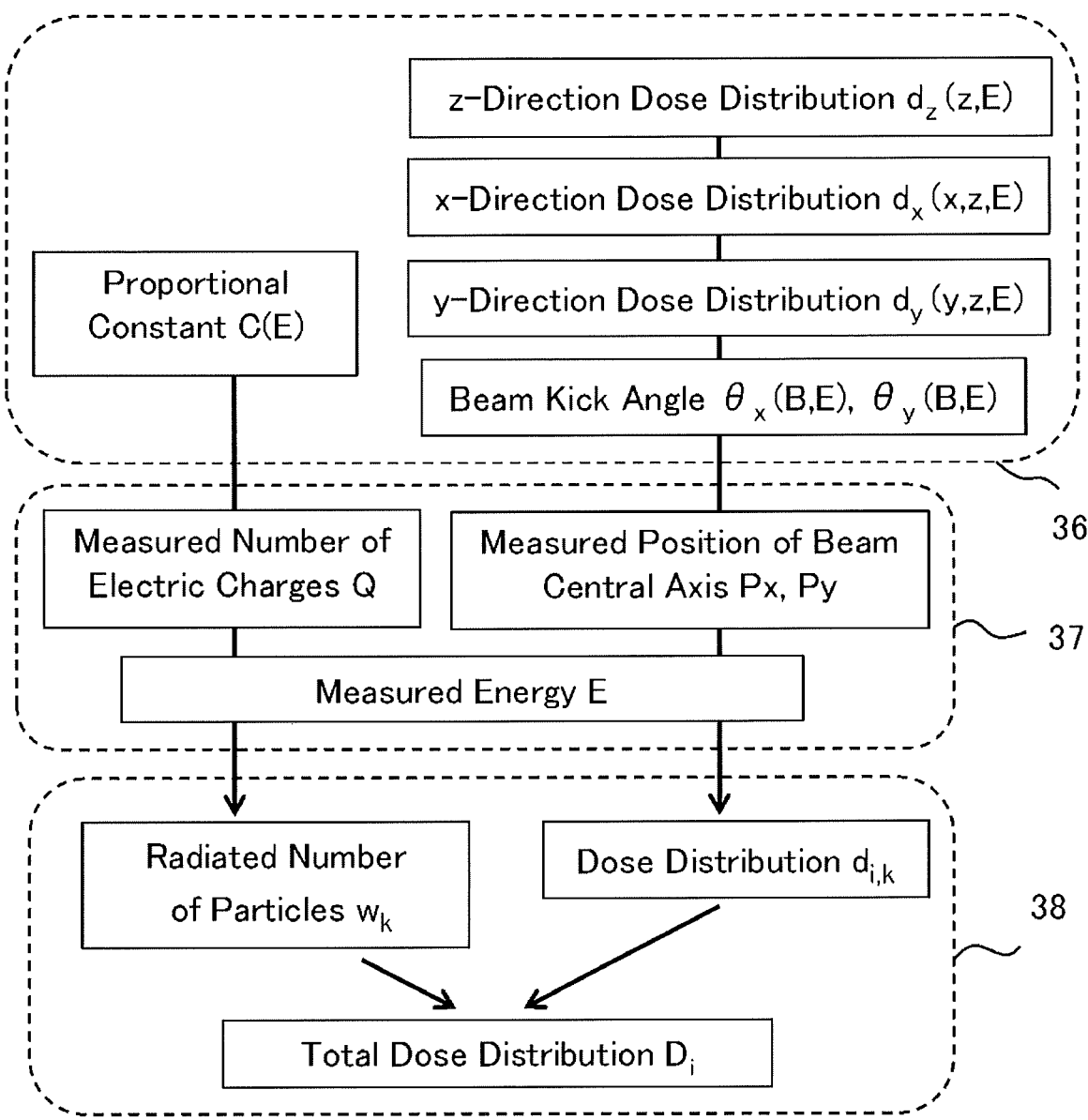
FIG. 6 is a diagram illustrating a flow of a patient QA according to Embodiment 1 of the invention.

FIG. 1 is a schematic configuration diagram of a particle beam irradiation apparatus at the time a patient QA is executed, according to Embodiment 1 of the invention. FIG. 2 is a diagram showing a configuration of a dose distribution calculation device in FIG. 1, and FIG. 3 is a diagram showing a hardware configuration by which functional blocks in FIG. 2 are implemented. FIG. 4 is a diagram showing an example of a structure of data to be inputted to the dose distribution calculation device in FIG. 1, and FIG. 5 is a diagram illustrating an example of a total dose distribution and dose evaluation points in a patient QA, according to Embodiment 1 of the invention. FIG. 6 is a diagram illustrating a flow of a patient QA according to Embodiment 1 of the invention. In general, a particle beam therapy system 50 for executing particle-beam scanning irradiation includes: a particle beam generation apparatus 1 for generating a particle beam 20 with energy required for therapy; a beam transport apparatus 2 for transporting the particle beam 20 to a particle beam irradiation apparatus provided with a scanning device 3; and the scanning device 3 that can scan the particle beam 20 at the place of a patient, by deflecting the particle beam 20 in two directions perpendicular to a z-direction that is a beam traveling direction, namely, in an x-direction and a y-direction.

The scanning device 3 includes: an x-direction scanning electromagnet 4 for deflecting the particle beam 20 in the x-direction; and a y-direction scanning electromagnet 5 for deflecting the particle beam 20 in the y-direction. The particle beam therapy system 50 includes: a control unit (not shown) for controlling initiation and interruption of radiation of the particle beam 20 by the particle beam generation apparatus 1, and scanning of the particle beam 20 by the scanning device 3; a dose measuring device 7 for measuring a dose value at each irradiation position in the treatment target (patient) to which the particle beam scanned by the scanning device 3 is radiated; and a position monitor (not shown) for detecting beam information used for calculating a beam passing position (gravity center position) through which the charged particle beam 20 scanned by the x-direction scanning electromagnet 4 and the y-direction scanning electromagnet 5 passes, and a size of the beam.

At the time a patient QA is executed, as shown in FIG. 1, a phantom 21 is placed at a position where a patient is to be fastened at the time of treatment. The particle beam therapy system 50 at the time the patient QA is executed includes: the particle beam generation apparatus 1; the beam transport apparatus 2; the scanning device 3; a beam energy measuring device 6; the dose measuring device 7; a beam-central axis measuring device 8; and a dose distribution calculation device 10. The beam energy measuring device 6 measures the energy of the particles in the particle beam 20. The beam energy measuring device 6 is, for example, a thin-film scintillation detector or the like. The dose measuring device 7 at the time the patient QA is executed is, for example, an ionization chamber, which measures the number of electric charges (unit-charge count value) of ionized ions generated by the particle beam 20. The number of electric charges of the ionized ions has one-to-one correspondence with the beam quantity of the particle beam 20. The beam-central axis measuring device 8 measures positions x, y of the beam central axis established by the x-direction scanning electromagnet 4 and the y-direction scanning electromagnet 5. Specifically, the beam-central axis measuring device 8 measures the beam-central axis positions x, y that are positions of the beam central axis, through calculation based on an intensity B of magnetic field induced on the pathway of the particle beam 20 by the scanning device 3. The beam-central axis position x is a position in the x-direction, and the beam-central axis position y is a position in the y-direction. The dose distribution calculation device 10 calculates a dose distribution on the basis of: respective measured energies E(t) measured at multiple time points for a specified time interval Δt, for example, by the dose energy measuring device 6; respective measured numbers of electric charges Q(t) (measured beam quantities) measured at the multiple time points by the dose measuring device 7; and respective measured positions of beam central axis Px(t), Py(t) measured at the multiple points by the beam-central axis measuring device 8. An energy E, a measured beam quantity (measured number of electric charges Q) and a measured position of beam central axis Px, Py, of the particle beam 20, are particle beam information of the particle beam 20. The measured energies E(t), the measured beam quantities (measured numbers of electric charges Q(t)), and the measured positions of beam central axis Px(t), Py(t), are measured particle beam information.

The dose distribution calculation device 10 includes: a database 11 in which five types of information written in database information 36 in FIG. 6 are stored; a measured electric-charge storing unit 12 in which the measured numbers of electric charges Q(t) are stored; a measured beam-central axis storing unit 13 in which the measured positions of beam central axis Px(t), Py(t) are stored; a measured energy storing unit 14 in which the measured energies E(t) are stored; a total dose calculation unit 15; a planned dose comparison unit 16; and an alarm display unit 18, such as a display, an alarm lamp, etc., for indicating warning. The total dose calculation unit 15 and the planned dose comparison unit 16 are implemented in such a manner that a processor 98 executes programs stored in a memory 99. Instead, plural processors 98 and plural memories 99 may execute the above functions in their cooperative manner. Details of the dose distribution calculation device 10 will be described later.

Firstly, a total dose to be imparted by scanning irradiation to a tumor volume (tumor region) will be described. In scanning irradiation, multiple spots are set up in the tumor volume (tumor region), and an adequate quantity of the particle beam 20 is radiated to each of the spots, so that an intended total dose distribution 25 is established as shown, for example, in FIG. 5. When a spot number is defined as j, a dose-evaluation point number in the phantom 21 is defined as i, a dose to be imparted to i-th dose-evaluation point pi when one particle is radiated to j-th spot is defined as $d_{i,j}$, a number of particles to be given to j-th spot is defined as $w_j$, and a total number of spots is defined as n, a total dose $D_i$ to be imparted to i-th dose-evaluation point pi after completion of radiation to all the spots, can be represented as a formula (1).

[Mathematical 1]

$$D_i = \sum_{j=1}^{n} w_j d_{i,j} \qquad (1)$$

Such a process is required that calculates, before radiation, an optimum number of particles $w_j$ to be given to the spot so that the total dose $D_i$ at each dose-evaluation point pi is as close as possible to a target dose distribution. This process is referred to as treatment planning. Where appropriate, the number of particles $w_j$ is referred to as the number of spot-particles $w_j$.

FIG. 5 shows an example of the number and positions of spots and the number of spot-particles $w_j$ that are determined to be applied in execution of the treatment planning. In FIG. 5, the ordinate represents a dose, and the abscissa represents a position in the z-direction. In FIG. 5, for simplification's sake, a one-dimensional example is shown in which the spot arrangement and also the dose distribution are in a direction of the z-axis (beam traveling direction). In FIG. 5, four spots of sp1, sp2, sp3 and sp4, and thirteen dose-evaluation points of p1, p2, p3, p4, p5, p6, p7, p8, p9, p10, p11, p12 and p13, are shown. A dose distribution 26 is a dose distribution according to the number of spot-particles radiated to the spot sp1. Likewise, dose distributions 27, 28 and 29 are dose distributions according to the numbers of spot-particles radiated to the spots sp2, sp3 and sp4, respectively. The total dose distribution 25 is a dose distribution resulting from adding together the dose distributions 26, 27, 28 and 29. There are eight dose-evaluation points in the tumor that are the dose-evaluation points of p3 to p10. There are five dose-evaluation points outside the tumor that are the dose-evaluation points of p1, p2 and p11 to p13.

As shown in FIG. 5, when the number of particles $w_j$ to be given to each of the spots sp1 to sp4 is determined adequately, it is possible to make the total dose distribution 25 higher in the tumor and lower outside the tumor. Although the number of spots is four and the number of dose-evaluation points is thirteen in FIG. 5, much more spots and dose-evaluation points are generally positioned with short intervals, in conformity with the size of the tumor. Further, in FIG. 5, for simplification's sake, the spot arrangement and also the dose distribution are only shown one-dimensionally in the z-axis direction; however, the spots are actually positioned three-dimensionally in the directions further including the x-axis direction and the y-axis direction, in conformity with the shape of the tumor. The dose distribution is also required to be calculated on a three-dimensional basis in conformity with an actual shape of the tumor, so that the dose-evaluation points are positioned three-dimensionally.

In general, spot positions in the x-direction and the y-direction that are directions perpendicular to the beam traveling direction (z-direction) are determined by a beam kick angle, and the beam kick angle is determined depending on the intensity of a magnetic field formed by the scanning device 3. Further, a spot position in the z-direction that is the beam traveling direction is determined depending on the beam energy of the particle beam 20. Accordingly, the particle beam therapy system 50 adjusts these spot positions by adjusting the beam energy of the particle beam 20 and the intensity of the magnetic field by the scanning device 3.

According to the formula (1), the dose distributions for the respective spots are added together, so that a total dose distribution at i-th dose-evaluation point pi is calculated. The total dose distribution after completion of radiation of the particle beam 20 to a common target can be determined in an adding manner for every time, and can thus be calculated, like the formula (1), as shown by a formula (2).

[Mathematical 2]

$$D_i = \sum_{k=1}^{m} w_k d_{i,k} \quad (2)$$

Here, the formula (2) represents a case in which the total radiation time is divided into m time segments. Indicated by k is a time segment number. A number of particles radiated to i-th dose-evaluation point pi in k-th time segment is defined as $w_k$, and a dose (unit particle dose) to be imparted to i-th dose-evaluation point pi when one particle in the beam is assumed to be radiated to an average position of the beam staying in k-th time segment, is defined as $d_{i,k}$. When the time interval is shortened sufficiently, the formula (2) can reproduce the dose distribution highly accurately. Here, the time interval is desired to be the same level of, or shorter than, a required time per one spot and, for example, a level of from several tens of microseconds to one millisecond is thought to be preferable. When the number of particles $w_k$ and the unit particle dose $d_{i,k}$ in a common time segment are multiplied together, the resultant $w_k \cdot d_{i,k}$ represents a time-segmental dose.

The number of particles $w_k$ radiated in a given time segment can be measured, for example, by the dose measuring device 7 using an ionization chamber. The ionization chamber is generally an instrument that outputs an electric signal when the particle beam 20 passes therethrough, and there is a proportional relationship between the number of particles in the passed particle beam 20 and the number of electric charges (unit-charge count value) of the ionized ions generated. Accordingly, when a total number of electric charges generated from the start to the end of a given time segment is defined as $Q_k$, and a proportional constant between the total number of electric charges $Q_k$ and the number of particles $W_k$ in the particle beam 20 is defined as C(E), the number of particles $w_k$ can be calculated in a manner according to a formula (3). Since the total number of electric charges $Q_k$ represents a beam quantity, the proportional constant C(E) can be said to be a ratio of the number of particles $w_k$ relative to the beam quantity. Note that, where appropriate, the number of particles $w_k$ is referred to as the radiated number of particles $w_k$.

[Mathematical 3]

$$w_k = C(E) Q_k \quad (3)$$

Here, the symbol E represents the energy of the particles in the particle beam 20. The proportional constant is generally dependent on the energy, so that the proportional constant is provided as an expression including the energy E of the particles in the particle beam 20.

It is required that the proportional constant C(E) be acquired in advance before execution of QA radiation (confirmative radiation) in which the particle beam 20 is radiated for the patient QA to the phantom 21. In an example of the acquiring method, a reference ionization chamber with an already-known proportional constant between a total number of electric charges $Q_{kr}$, and a number of particles $W_{kr}$, and a QA ionization chamber to be actually employed at the time of QA radiation, are set up, so that the proportional constant C(E) can be calculated by comparison between their measured values. Specifically, the reference ionization chamber is placed on the downstream side of the QA ionization chamber, and an adequate quantity of the particle beam 20 with a constant energy E is radiated to them, so that the proportional constant C(E) for that energy can be calculated from the ratio between the number of particles $w_k$ according to the output of the QA ionization chamber and the number of particles $w_{kr}$ determined according to the output of the reference ionization chamber. When similar measurements are executed while changing the energy E, it is possible to find the proportional constant C(E) for any given energy E.

It is ideal that the measurement using the reference ionization chamber and the QA ionization chamber be executed for every energy E possibly used for the treatment, followed by acquisition of every C(E) and storing of them as a database. However, in order to save trouble in measurement, such a method is conceivable that executes the measurement for only some energies E, followed by linear interpolation between the energies, to thereby obtain a function of the proportional constant C(E). For this case, it is required that the approximation accuracy by use of the interpolation be well verified and understood.

The energy E of the particles in the particle beam 20 can be measured using the beam energy measuring device 6, for example, a thin-film scintillation detector or the like. In such a case where a curved section exists in the pathway along which the beam is transported from the particle beam generation apparatus 1 to the patient or the phantom 21, such a beam energy measuring device 6 is conceivable as another example that employs a method using a magnetic field of a deflection electromagnet placed at the curved section in the beam pathway. Specifically, the beam energy can be calculated from the relationship between the intensity of the magnetic field created by the deflection electromagnet placed at the curved section in the beam pathway, and the curvature radius in the beam pathway.

When the dose-evaluation points for the formula (2) are three-dimensionally provided, the dose $d_{i,k}$ can be calculated in the following manner. It is known that a three-dimensional dose distribution $d(x,y,z)$ can be approximated by a product of a dose distribution in the z-direction, a dose distribution in the x-direction and a dose distribution in the y-direction. In the paper of Inaniwa, et al. (Non-Patent Document 1), such a method is presented in which the three-dimensional dose distribution $d(x,y,z)$ with respect to one beam is factorized into the respective dose distributions in the z-direction, the x-direction and the y-direction, as shown in a formula (4).

[Mathematical 4]

$$d(x,y,z)=d_z(z,E) \times d_x(x-x_0,z,E) \times d_y(y-y_0,z,E) \quad (4)$$

Here, $x_0$ and $y_0$ represent coordinates of a central axis of one beam at a depth z. As can be seen from the formula (4), the dose distribution in the z-direction is determined only by the coordinate in the z-direction and the beam energy E (energy E of the beam) without depending on the coordinate in the x-direction and the coordinate in the y-direction; however, the dose distributions in the x-direction and the y-direction vary according not only to the coordinate in the x-direction, the coordinate in the y-direction and the beam energy E, but also to the coordinate in the z-direction and the position $(x_0,y_0)$ of the beam central axis. As previously described, similarly to the manner of adding together the dose distributions for the respective spots, the dose distribution after completion of radiation of the particle beam 20 to the common target can be determined in an adding manner for every time. Thus, the dose $d_{i,k}$ when the dose-evaluation points are three-dimensionally provided can be represented as a formula (5) using factorization into the respective doses in the z-direction, the x-direction and the y-direction.

[Mathematical 5]

$$d_{i,k}=d_z(z,E) \times d_x(x,z,E) \times d_y(y,z,E) \quad (5)$$

It is noted that, for any arbitrary z-coordinate, $d_z(z,E)$ represents a dose distribution in the z-direction, but for a unique z-coordinate, it represents a value of dose at that z-coordinate, so that "dose distribution" and "dose" are used differently depending on whether the z-coordinate is used arbitrarily or uniquely. The same applies to $d_x(x,z,E)$ and $d_y(y,z,E)$, and thus, for any arbitrary (x,y)-coordinate, they represent dose distributions in the x-direction and in the y-direction, respectively, but for a unique (x,y)-coordinate, they represent values of doses at that (x,y)-coordinate, so that "dose distribution" and "dose" are used differently depending on whether the (x,y)-coordinate is used arbitrarily or uniquely. For i-th dose-evaluation point pi, its coordinate (x,y,z) has been uniquely determined, so that $d_z(z,E)$, $d_x(x,z,E)$ and $d_y(y,z,E)$ represent a dose in the z-direction, a dose in the x-direction and a dose in the y-direction, respectively. When any arbitrary i-th dose-evaluation point pi is instead focused on, they are referred to as dose distributions in their respective directions. Further, for $D_i$ and $d_{i,k}$, similarly, "dose distribution" and "dose" are used differently depending on whether the dose-evaluation point is used arbitrarily or uniquely. They are referred to as a total dose $D_i$ and a dose $d_{i,k}$ when used for a unique dose-evaluation point, but referred to as a total dose distribution $D_i$ and a dose distribution $d_{i,k}$ when used for any arbitrary dose-evaluation point.

The position of beam central axis in the formula (4) can also be calculated through analytical calculation based on Lorentz force represented by a formula (6).

[Mathematical 6]

$$f=qvB \quad (6)$$

Here, q, v and B in the formula (6) represent electric charges of the particles, a velocity of the particles, and a magnetic flux density of the magnetic field applied to the particles, respectively. Note that, only for the description of the formula (6) and the Lorentz force, the symbol B is described as the magnetic flux density.

The position of beam central axis may be put into a database after it is directly measured beforehand. Namely, the position monitor is placed at the downstream side of the scanning device 3, a magnetic field with a given magnetic flux density B is induced, and the particle beam 20 is radiated with a given beam energy E, and then the position through which the beam central axis passes is measured, so that a kick angle θ of the particle beam 20 is found from the distance between locations of the scanning device 3 and the position monitor. According to the kick angle of the beam, it is possible to calculate the x-coordinate and the y-coordinate at an arbitrary position z (z-coordinate) and with reference to the beam central axis. It is ideally desired that the measurement of the kick angle θ of the beam be also executed beforehand for every energy E and every magnetic field intensity B that are possibly used for the treatment; however, in order to save trouble, linear interpolation may be used after acquisition of only some data. With respect, in particular, to the magnetic field intensity B, a linear relationship between the magnetic field intensity B and the kick angle θ is promising from the definition of Lorentz force, so that the accuracy can expect not to decrease even if the interpolation is applied with some omission of measurement. Note that a kick angle θ in the x-direction is represented as $θ_x$, and a kick angle θ in the y-direction is represented as $θ_y$. In addition, since the kick angle θ depends on the magnetic field intensity B and the position z (z-coordinate), where appropriate, the kick angle $θ_x$ is represented as $θ_x(B,E)$, and the kick angle $θ_y$ is represented as $θ_y(B,E)$.

With respect to the dose distribution $d_z(z,E)$ in the z-direction in the formula (4) and the formula (5), although it can be calculated based on the theory known as the Bragg formula, it is thought to be most convenient that the distribution be actually measured beforehand using a water phantom (phantom 21) and a dosimeter, and put into a database. When it is to be measured beforehand, water is poured in the water phantom and the dosimeter is placed therein, so that it is possible to achieve the distribution by shifting the position of the dosimeter in the z-direction while radiating the particle beam 20. If, prior to execution of this measurement, the measurement for acquiring the proportional constant C(E) has been executed, it is possible, by placing the QA ionization chamber for that execution on the upstream side, to achieve the radiated number of particles w and the dose d in the water phantom. Then, by calculating the ratio therebetween, it is possible to find the dose distribution $d_z(z,E)$ per one particle.

With respect to the dose distribution $d_x(x-x_0,z,E)$ in the formula (4) and the dose distribution $d_x(x,z,E)$ in the formula (5), they can be calculated based on the multiple scattering theories by Moliere and Fermi-Eyges, Highland, et al. Instead, it is also allowable to actually measure them beforehand using a water phantom (phantom 21) and a dosimeter, and put them into a database. It is required that this measurement be executed for all x and z, because the dose distribution varies depending on both x and z in comparison with the measurement of the dose distribution $d_z(z,E)$. But, this provides a lot of trouble. Thus, Monte-Carlo Simulation Tool is used that is known as Geant4 or the like, so that a dose per one particle at any position in the water phantom (phantom 21) can be calculated. Specifically, when Monte-Carlo Simulation is to be executed, information is inputted that includes: the shapes of objects such as the phantom 21 and the like; the energy of the particle beam 20; the position and direction where ionization occurs; the position of beam central axis deflected by the electromagnets (x-direction scanning electromagnet 4, y-direction scanning electromagnet 5) in the scanning device 3; and the like; so that a dose per one particle at any position in the water phantom (phantom 21) can be calculated. Accordingly, execution of Monte-Carlo Simulation makes it possible to achieve the dose distribution $d_x(x-x_0, z, E)$ and the dose distribution $d_x(x,z,E)$ in the x-direction, more efficiently than by actual measurement. The same applies to dose distributions in the y-direction, namely, the dose distribution $d_y(y-y_0,z,E)$ in the formula (4) and the dose distribution $d_y(y,z,E)$ in the formula (5).

When Monte-Carlo Simulation Tool is used, it is possible not only to calculate the dose distributions each in one-dimensional direction, but also to directly calculate a three-dimensional distribution $d(x,y,z)$, so that such a method is also applicable in which that distribution is calculated beforehand and the information of $d(x,y,z)$ is held as a database. However, a large amount of memory is required to store in a storage device, each dose distribution that extends three-dimensionally, and thus, it is necessary to assess what form the data is preferably held in, in consideration of the ability of the storage device and the required accuracy for the data.

Using FIG. 6, the flow of a patient QA according to the invention will be described. Firstly, prior to the start of the patient QA (at the time of launching the facility or the like), as advance preparation, such an operation (database preparation step) is required that acquires the necessary data using the methods described so far, and then prepares the database 11 in which five types of information written in the database information 36 are stored. A first database is for the constant for converting the measured number of electric charges Q(t) that is the output number of electric charges by the dose measuring device 7, into the number of particles w, namely, the proportional constant $C(E)$. A second database is for the dose distribution $d_z(z,E)$ in the z-direction. A third database is for the dose distribution $d_x(x,z,E)$ in the x-direction. A fourth database is for the dose distribution $d_y(y,z,E)$ in the y-direction. A fifth database is for a conversion table between the intensity B of magnetic field formed by the electromagnets (x-direction scanning electromagnet 4, y-direction scanning electromagnet 5) in the scanning device 3, and the kick angles $\theta_x(B,E)$, $\theta_y(B,E)$ of the particle beam 20.

Next, at the time the treatment is actually applied to the patient, the patient is firstly subjected to CT imaging, so that the position and the shape of the tumor are determined, and thereafter, preparation of the treatment plan is executed by a treatment planning apparatus (treatment plan preparation step). What follows is the flow in which the particle beam 20 is radiated to the patient on the basis of the treatment plan (treatment radiation step); however, at some time in the period after the preparation of the treatment plan and before the radiation to the patient, a patient QA operation (patient QA step) will be required. It is generally thought that, in many cases, the patient QA is performed on the day just before the radiation to the patient; however, this is not necessarily required.

At the time of the patient QA, on the basis of the number of particles $w_j$ per spot indicated by the treatment plan, the particle beam 20 is radiated to the phantom 21 (QA radiation step). This QA radiation step is a step of performing confirmative radiation, so that it may also be referred to as a confirmative radiation step. During radiation of the beam, the measured numbers of electric charges Q, the measured positions of beam central axis Px, Py, and the measured energies E, that are three respective measured values written in measured-value information 37 are subjected to measurement for predetermined respective time segments $\Delta t$ (QA-data measuring step). The measured numbers of electric charges Q (measured beam quantities) are all data about the measured number of electric charges Q(t) (information of the measure beam quantity) that is the number of electric charges according to the dose measuring device 7 and is measured in every time segment $\Delta t$. The measured positions of beam central axis Px, Py are all data about the measured position of beam central axis Px(t), Py(t) that corresponds to the magnetic field by the x-direction scanning electromagnet 4 and the y-direction scanning electromagnet 5 in the scanning device 3 and is measured in every time segment $\Delta t$. The measured energies E are all data about the measured energy E(t) that is the beam energy of the particle beam 20 and is measured in every time segment $\Delta t$.

The measured numbers of electric charges Q, the measured positions of beam central axis Px, Py and the measured energies E are stored in the measured electric-charge storing unit 12, the measured beam-central axis storing unit 13 and the measured energy storing unit 14, respectively. Since the measured number of electric charges Q is also referred to as the measured beam quantity, so that the measured electric-charge storing unit may also be referred to as a measured beam-quantity storing unit. The measured numbers of electric charges Q, the measured positions of beam central axis Px, Py and the measured energies E may be grouped together as shown in the data structure of measured-value stored information 35 illustrated in FIG. 4. At a time point t1 that represents the first segment for measurement, the measured number of electric charges Q(t1), the measured energy E(t1) and the measured position of beam central axis Px(t1), Py(t1) are subjected to measurement. At a time point t2 after the elapse of the time segment $\Delta t$, the measured number of electric charges Q(t2), the measured energy E(t2) and the measured position of beam central axis Px(t2), Py(t2) are subjected to measurement. Likewise, every time the time segment $\Delta t$ elapses, the measured number of electric charges Q(t), the measured energy E(t) and the measured position of beam central axis Px(t), Py(t) are subjected to measurement. At a time point tn that represents the last segment for measurement, the measured number of electric charges Q(tn), the measured energy E(tn) and the measured position of beam central axis Px(tn), Py(tn) are subjected to measurement. Note that the measured electric-charge storing unit 12, the measured beam-central axis storing unit 13 and the measured energy storing unit 14 may not be provided as internal storing regions of the dose distribution calculation device 10 and thus may be provided as external storing regions.

After the QA radiation, the dose distribution calculation device 10 calculates the total dose distribution $D_i$ in the phantom 21 (total dose-distribution calculation step), on the basis of: the respective types of information (the measured numbers of electric charges Q, the measured positions of beam central axis Px, Py, and the measured energies E) stored in the measured electric-charge storing unit 12, the measured beam-central axis storing unit 13 and the measured energy storing unit 14; and the information in the database 11. In the total dose-distribution calculation step, the radiated number of particles $w_k$, the dose distribution $d_{i,k}$ and the total dose distribution $D_i$, that are three items written in calculation result information 38, are calculated. According to the formula (3), in every segment for measurement, the total dose calculation unit 15 calculates the radiated number of particles $w_k$ from the proportional constant C(E) and the measured number of electric charges Q(t) that corresponds to the total number of electric charges $Q_k$. Further, according to the formula (5), the total dose calculation unit 15 calculates the dose distribution $d_{i,k}$ on the basis of the measured position of beam central axis Px, Py, and the z-direction dose distribution $d_z(z,E)$, the x-direction dose distribution $d_x(x,z,E)$ and the y-direction dose distribution $d_y(y,z,E)$ that are selected according to the measured energy E.

Calculation operations of the total dose calculation unit 15 will be detailed. The total dose calculation unit 15 reads out from the database 11, the proportional constant C(E) corresponding to the measured energy E, and multiplies the measured number of electric charges Q(t) by the proportional constant C(E), to thereby calculate the radiated number of particles $w_k$. Further, how to calculate the dose distribution $d_{i,k}$ in the total dose calculation unit 15 will be described citing i-th dose evaluation point pi as an example. The total dose calculation unit 15 derives from the z-direction dose distribution $d_z(z,E)$ in the database 11, the z-direction dose that corresponds to the z-coordinate of i-th dose evaluation point pi and to the measured energy E, namely, a selected z-direction dose $d_z$.

The total dose calculation unit 15 derives from among the beam kick angles $\theta_x(B,E)$, $\theta_y(B,E)$ in the database 11, the x-direction kick angle (selected x-direction kick angle) $\theta_x$ and the y-direction kick angle (selected y-direction kick angle) $\theta_y$ that correspond to the measured position of beam central axis Px, Py and the measured energy E. The total dose calculation unit 15 calculates the x-coordinate from the x-direction kick angle $\theta_x$ and derives from the x-direction dose distribution $d_x(x,z,E)$ in the database 11, the x-direction dose (selected x-direction dose) $d_x$ that corresponds to that x-coordinate, the z-coordinate of the dose evaluation point and the measured energy E. Likewise, the total dose calculation unit 15 calculates the y-coordinate from the y-direction kick angle $\theta_y$ and derives from the y-direction dose distribution $d_y(y,z,E)$ in the database 11, the y-direction dose (selected y-direction dose) $d_y$ that corresponds to that y-coordinate, the z-coordinate of the dose evaluation point and the measured energy E.

On the basis of the derived z-direction dose $d_z$, x-direction dose $d_x$ and y-direction dose $d_y$, the total dose calculation unit 15 multiples together the three doses $d_z$, $d_x$, $d_y$ according to the formula (5) to thereby calculate the dose $d_{i,k}$. The total dose calculation unit 15 calculates the dose $d_{i,k}$ for every dose valuation point and time segment, to thereby determine the dose distribution $d_{i,k}$. On the basis of the already-calculated radiated number of particles $w_k$ and dose distribution $d_{i,k}$, the total dose calculation unit 15 calculates the total dose distribution $D_i$ according to the formula (2).

Further, the dose distribution calculation device 10 compares, in the planned dose comparison unit 16, the calculated total dose distribution $D_i$ with a dose distribution (planned dose distribution) $D_{ip}$ outputted by the treatment planning apparatus. According to Non-Patent Document 2, for example, it is recommended that administered-dose accuracy be within ±3% for the region of a tumor and ±4% for the region outside the tumor. The planned dose comparison unit 16 compares these doses at all of the dose evaluation points pi to thereby calculate the administered-dose accuracy as shown in a formula (7).

$$\text{Administered-Dose Accuracy} = (D_i - D_{ip})/D_{ip} \qquad (7)$$

If there is any dose evaluation point where the calculated administered-dose distribution exceeds the above criteria, the planned dose comparison unit 16 displays an alarm on the alarm display unit 18.

As described above, the dose distribution calculation device 10 of Embodiment 1 is a dose distribution calculation device 10 for calculating, when the particle beam therapy system 50 performs a particle beam therapy by scanning, using the scanning device 3, the particle beam 20 on a treatment target, a radiation dose distribution (total dose distribution $D_i$) to be applied by the particle beam therapy system 50 to the treatment target, said dose distribution calculation device characterized by comprising: the beam information storing unit (the measured energy storing unit 14, the measured beam-quantity storing unit (measured electric-charge storing unit 12) and the measured beam-central axis storing unit 13) in which, when particle beam information of the particle beam 20 generated by the particle beam therapy system 50 is measured by the measuring device (the beam energy measuring device 6, the dose measuring device 7 and the beam-central axis measuring device 8) in confirmative radiation in which the particle beam 20 is radiated to the phantom 21 as a substitute for the treatment target, the thus-measured particle beam information is stored; and the total dose calculation unit 15 for calculating the radiation dose distribution on the basis of the measured particle beam information (the measured energy E, the measured beam quantity (measured number of electric charges Q) and the measured position of beam central axis Px, Py). According to the dose distribution calculation device 10 of Embodiment 1, because of these characteristics, the radiation dose distribution is calculated based on the measured particle beam information, so that it is possible to accomplish a patient QA which requires no dose detector having high positional resolution and requires no measurement of doses at many points in the phantom 21, and in which both the static and dynamic uncertainties are eliminated.

Further, in the dose distribution calculation device 10 of Embodiment 1, the particle beam information includes a beam quantity, an energy and a position of beam central axis, of the particle beam 20, and the beam information storing unit includes: the measured energy storing unit 14 for storing respective measured energies E(t) resulting from measuring the energy of the particle beam 20 at multiple time points during the confirmative radiation; the measured beam-central axis storing unit 13 for storing respective measured positions of beam central axis Px(t), Py(t) resulting from measuring the position of beam central axis of the particle beam 20 at multiple time points during the confirmative radiation; and the measured beam-quantity storing unit (measured electric-charge storing unit 12) for storing respective measured beam quantities (measured numbers of electric charges Q(t)) resulting from measuring the beam quantity of the particle beam 20 at multiple time points during the confirmative radiation. The total dose calculation unit 15 in the dose distribution calculation device 10 of Embodiment 1 is characterized in that it calculates a dose at a calculation target point (dose evaluation point pi) in the treatment target, by adding together every time-segmental dose therefor, over all of the time segments in each of which the particle beam information is measured, said every time-segmental dose resulting from multiplying the radiated number of particles $w_k$ calculated based on the measured energy E(t) and the measured beam quantity (measured number of electric charges Q(t)) in a common segment in the time segments, by the unit particle dose (dose $d_{i,k}$) that is a dose to be imparted by one particle in the particle beam 20 and that is calculated based on the measured energy E(t) and the measured position of beam central axis Px(t), Py(t) in the common segment in the time segments. According to the dose distribution calculation device 10 of Embodiment 1, because of these characteristics, the total dose calculation unit 15 calculates the radiation dose distribution on the basis of the measured energy E(t), the measured position of beam central axis Px(t), Py(t) and the measured beam quantity (measured number of electric charges Q(t)) in each of the time segments, so that it is possible to accomplish a patient QA which requires no dose detector having high positional resolution and requires no measurement of doses at many points in the phantom 21, and in which both the static and dynamic uncertainties are eliminated.

The dose distribution calculation method of Embodiment 1 is a dose distribution calculation method of calculating, when the particle beam therapy system 50 performs a particle beam therapy by scanning using the scanning device 3 the particle beam 20 on a treatment target, a radiation dose distribution (total dose distribution $D_i$) to be applied by the particle beam therapy system 50 to the treatment target, said dose distribution calculation method characterized by comprising: the confirmative radiation step (QA radiation step) of radiating the particle beam 20 to the phantom 21 as a substitute for the treatment target; the data measuring step (QA-data measuring step) of measuring the energy, the beam quantity and the position of beam central axis, that are particle beam information of the particle beam 20 generated by the particle beam therapy system 50, at multiple time points during the confirmative radiation step (QA radiation step), to thereby collect the respective measured energies E, the respective measured beam quantities (measured numbers of electric charges Q) and the respective measured positions of beam central axis Px, Py; and the total dose-distribution calculation step of calculating the radiation dose distribution (total dose distribution $D_i$) on the basis of the measured energy E(t), the measured position of beam central axis Px(t), Py(t) and the measured beam quantity (measured number of electric charges Q(t)), in each common segment in the time segments. The dose distribution calculation method of Embodiment 1 is characterized in that, in the total dose-distribution calculation step, a dose at a calculation target point (dose evaluation point pi) in the treatment target is calculated by adding together every time-segmental dose therefor, over all of the time segments, said every time-segmental dose resulting from multiplying the radiated number of particles $w_k$ calculated based on the measured energy E(t) and the measured beam quantity (measured number of electric charges Q(t)) in a common segment in the time segments, by a unit particle dose (dose $d_{i,k}$) that is a dose to be imparted by one particle in the particle beam and that is calculated based on the measured energy E(t) and the measured position of beam central axis Px(t), Py(t) in the common segment. According to the dose distribution calculation method of Embodiment 1, because of these characteristics, it is possible to accomplish a patient QA which requires no dose detector having high positional resolution and requires no measurement of doses at many points in the phantom 21, and in which both the static and dynamic uncertainties are eliminated.

The particle beam therapy system 50 of Embodiment 1 is characterized by comprising: the particle beam generation apparatus 1 for generating the particle beam 20 with energy required for particle beam therapy; the scanning device 3 for deflecting the particle beam 20 in two direction perpendicular to the beam traveling direction, to thereby scan the particle beam 20 at a place where an irradiation target is placed; the beam transport apparatus 2 for transporting the particle beam 20 to the scanning device 3; the beam energy measuring device 6 for measuring the energy of the particle beam 20 generated by the particle beam generation apparatus 1; the beam-central axis measuring device 8 for measuring the position of beam central axis through calculation based on the intensity of a magnetic field induced on the pathway of the particle beam 20 by the scanning device 3; the beam quantity measuring device (dose measuring device 7) for measuring the beam quantity of the particle beam 20 generated by the particle beam generation apparatus 1; and the dose distribution calculation device 10 for calculating the radiation dose distribution (total dose distribution $D_i$) to be applied by the particle beam 20 to the irradiation target. The dose distribution calculation device 10 in the particle beam therapy system 50 of Embodiment 1 is characterized by comprising: the beam information storing unit (the measured energy storing unit 14, the measured beam-quantity storing unit (measured electric-charge storing unit 12) and the measured beam-central axis storing unit 13) in which, when particle beam information of the particle beam 20 generated by the particle beam therapy system 50 is measured by the measuring device (the beam energy measuring device 6, the dose measuring device 7 and the beam-central axis measuring device 8) in confirmative radiation in which the particle beam 20 is radiated to the phantom 21 as a substitute for the treatment target, the thus-measured particle beam information is stored; and the total dose calculation unit 15 for calculating the radiation dose distribution on the basis of the measured particle beam information (the measured energy E, the measured beam quantity (measured number of electric charges Q) and the measured position of beam central axis Px, Py). According to the particle beam therapy system 50 of Embodiment 1, because of these characteristics, the radiation dose distribution is calculated based on the measured particle beam information, so that it is possible to accomplish a patient QA which requires no dose detector having high positional resolution and requires no measurement of doses at many points in the phantom 21, and in which both the static and dynamic uncertainties are eliminated.

Embodiment 2

Figure 7:
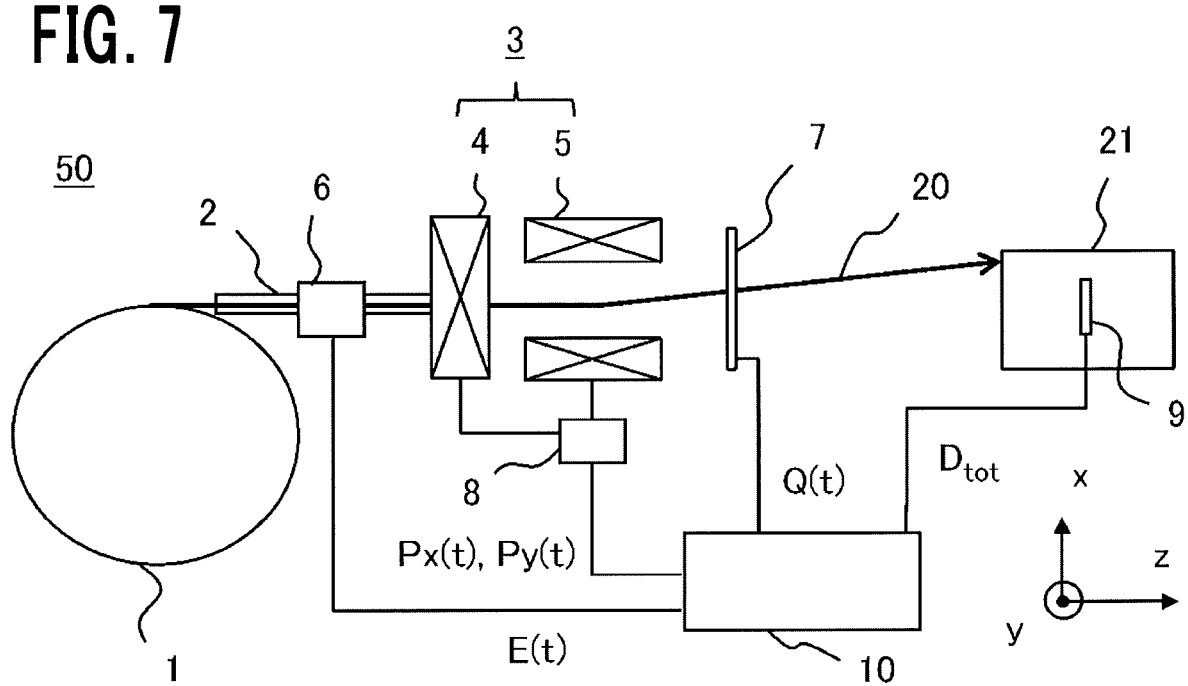
FIG. 7 is a schematic configuration diagram of a particle beam irradiation apparatus at the time a patient QA is executed, according to Embodiment 2 of the invention.
Figure 8:
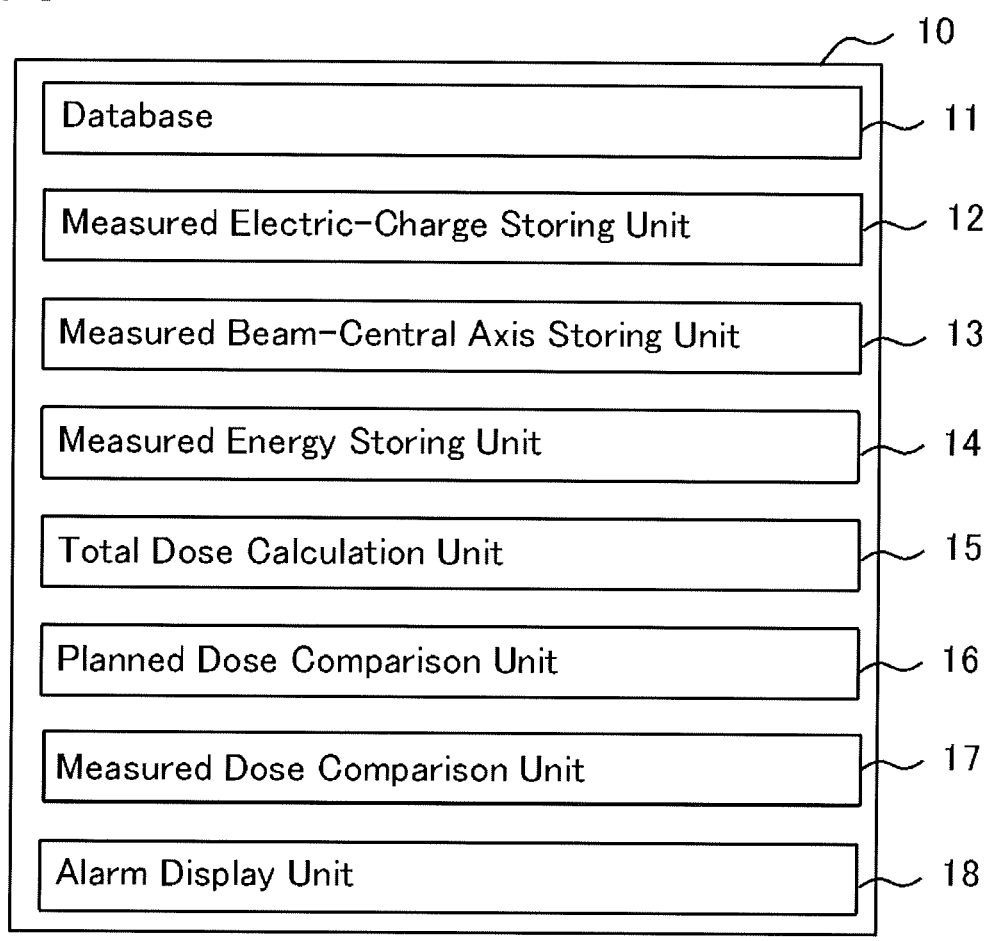
FIG. 8 is a diagram showing a configuration of a dose distribution calculation device in FIG. 7.

FIG. 7 is a schematic configuration diagram of a particle beam irradiation apparatus at the time a patient QA is executed, according to Embodiment 2 of the invention, and FIG. 8 is a diagram showing a configuration of a dose distribution calculation device in FIG. 7. A particle beam therapy system 50 of Embodiment 2 differs from the particle beam therapy system 50 of Embodiment 1 in that the dose distribution calculation device 10 comprises a measured dose comparison unit 17 for comparing a measured radiation dose $D_{tot}$ by a dose measuring device 9 placed in the phantom 21, with a calculated radiation dose $D_{totr}$ at the same coordinate in the dose distribution calculated by the total dose calculation unit 15. The measured dose comparison unit 17 is implemented in such a manner that the processor 98 shown in FIG. 3 executes a program stored in the memory 99. Instead, plural processors 98 and plural memories 99 may execute the above function in their cooperative manner.

At the time of preforming the QA radiation, the dose measuring device 9 is placed somewhere in the phantom 21 (for example, when a water tank is used as the phantom 21, at the center of the water tank). The dose measuring device 9 is, for example, an ionization chamber. By the dose measuring device 9, it is possible to measure an absolute value of the totalized radiation dose (absolute dose value irradiated) over all time segments in the QA radiation. At the measured dose comparison unit 17, the dose distribution calculation device 10 imports the measured radiation dose $D_{tot}$ that is a radiation dose measured by the dose measuring device 9, and compares the measured radiation dose $D_{tot}$ with the calculated radiation dose $D_{totr}$ outputted by the total dose calculation unit 15. The measured dose comparison unit 17 compares the value of the measured radiation dose $D_{tot}$ measured by the dose measuring device 9, with the value of the calculated radiation dose $D_{totr}$ at the same coordinate in the dose distribution outputted by the total dose calculation unit 15 in the dose distribution calculation unit 10. Then, the measured dose comparison unit 17 displays an alarm on the alarm display unit 18 if a difference between the value of the measured radiation dose $D_{tot}$ and the value of the calculated radiation dose $D_{totr}$ exceeds a criterion value (for example, ±3%).

According to the dose distribution calculation device 10 of Embodiment 2, in addition to an alarm based on the comparison by the planned dose comparison unit 16 between the total dose distribution $D_i$ and the dose distribution $D_{ip}$ from the treatment planning apparatus, it is possible to display an alarm based on the comparison by the measured dose comparison unit 17 between the value of the measured radiation dose $D_{tot}$ and the value of the calculated radiation dose $D_{totr}$. According to the dose distribution calculation device 10 of Embodiment 2, because it comprises the measured dose comparison unit 17, it is possible to execute a patient QA that is higher in accuracy than that in Embodiment 1. According to the particle beam therapy system 50 of Embodiment 2, because the dose distribution calculation device 10 comprises the measured dose comparison unit 17, it is possible to execute a patient QA that is higher in accuracy than that in Embodiment 1.

It should be noted that any combination of the respective embodiments, and any appropriate modification and omission in the embodiments may be made in the present invention without departing from the scope of the invention.

DESCRIPTION OF REFERENCE NUMERALS AND SIGNS

1: particle beam generation apparatus, 2: beam transport apparatus, 3: scanning device, 6: beam energy measuring device, 7: dose measuring device, 8: beam-central axis measuring device, 9: dose measuring device, 10: dose distribution calculation device, 11: database, 12: measured electric-charge storing unit (measured beam quantity storing unit), 13: measured beam-central axis storing unit, 14: measured energy storing unit, 15: total dose calculation unit, 16: planned dose comparison unit, 17: measured dose comparison unit, 20: particle beam, 21: phantom, 50: particle beam therapy system, pi: dose-evaluation point (calculation target point), E: measured energy, E(t): measured energy, Q: measured number of electric charges (measured beam quantity), Q(t): measured number of electric charges (measured beam quantity), Px, Py: measured position of beam central axis, Px(t), Py(t): measured position of beam central axis, C(E): proportional constant, $d_{i,k}$: dose (unit particle dose) or dose distribution, $w_k$: number of particles (radiated number of particles), $D_i$: total dose or total dose distribution (radiation dose distribution), $D_{ip}$: dose or dose distribution (planned dose distribution), $Q_k$: total number of electric charges (beam quantity), $D_{tot}$: measured radiation dose, $D_{totr}$: calculated radiation dose, $d_z$: z-direction dose (selected z-direction dose), $d_x$: x-direction dose (selected x-direction dose), $d_y$: y-direction dose (selected y-direction dose), $d_z(z,E)$: z-direction dose or dose distribution (z-direction dose distribution), $d_x(x,z,E)$: x-direction dose or dose distribution (x-direction dose distribution), $d_y(y,z,E)$: y-direction dose or dose distribution (y-direction dose distribution), $\theta_x$: x-direction kick angle (selected x-direction kick angle), $\theta_y$: y-direction kick angle (selected y-direction kick angle), $\theta_x(B,E)$: x-direction kick angle, $\theta_y(B,E)$: y-direction kick angle.

The invention claimed is:

1. A dose distribution calculation device for calculating, when a particle beam therapy system performs a particle beam therapy by scanning using a scanning device a particle beam on a treatment target, a radiation dose distribution to be applied by the particle beam therapy system to the treatment target, said dose distribution calculation device comprising:

a beam information storage in which, when particle beam information of the particle beam generated by the particle beam therapy system is measured by a measuring device in confirmative radiation in which the particle beam is radiated to a phantom as a substitute for the treatment target, the thus-measured particle beam information is stored; and a total dose calculator for calculating the radiation dose distribution on the basis of the measured particle beam information;

wherein the particle beam information includes a beam quantity, an energy and a position of beam central axis, of the particle beam;

wherein the beam information storage includes:

a measured energy storage for storing respective measured energies resulting from measuring the energy of the particle beam at multiple time points during the confirmative radiation;

a measured beam-central axis storage for storing respective measured positions of beam central axis resulting from measuring the position of beam central axis of the particle beam at multiple time points during the confirmative radiation; and a measured beam-quantity storage for storing respective measured beam quantities resulting from measuring a beam quantity of the particle beam at multiple time points during the confirmative radiation; and wherein the total dose calculator calculates a dose at a calculation target point in the treatment target, by adding together every time-segmental dose therefor, over all time segments in each of which the particle beam information is measured, said every time-segmental dose resulting from multiplying a radiated number of particles calculated based on the measured energy and the measured beam quantity in a common segment in the time segments, by a unit particle dose that is a dose to be imparted by one particle in the particle beam and that is calculated based on the measured energy and the measured position of beam central axis in the common segment in the time segments.

2. The dose distribution calculation device of claim 1, wherein the particle beam information includes a beam quantity of the particle beam, and the measured particle beam information includes a measured beam quantity.

3. The dose distribution calculation device of claim 1, wherein the measured particle beam information includes a measured energy.

4. The dose distribution calculation device of claim 1, wherein the particle beam information includes a position of beam central axis of the particle beam, and the measured particle beam information includes a measured position of beam central axis.

5. The dose distribution calculation device of claim 1, wherein the measured particle beam information includes a measured beam quantity, a measured energy and a measured position of beam central axis.

6. The dose distribution calculation device of claim 4, wherein the position of beam central axis is calculated based on an intensity of a magnetic field induced on a pathway of the particle beam by the scanning device.

7. The dose distribution calculation device of claim 1, wherein the particle beam information is measured at multiple time points during the confirmative radiation, so that the total dose calculator calculates a total dose distribution by adding together every dose distribution in each time segment.

8. The dose distribution calculation device of claim 1, further comprising a planned dose comparator for comparing the radiation dose distribution calculated by the total dose calculator, with a planned dose distribution that is a dose distribution outputted by a treatment planning apparatus, to thereby issue an alarm when a difference between the radiation dose distribution and the planned dose distribution at their common calculation target point in the treatment target, is more than an allowability determination value.

9. The dose distribution calculation device of claim 1, further comprising a measured dose comparator for comparing a dose value measured by a dosimeter placed in the phantom, with a calculated dose value in the radiation dose distribution calculated by the total dose calculator and corresponding to a placed position of the dosimeter, to thereby issue an alarm when a difference between these two dose values is more than an allowability determination value.

10. The dose distribution calculation device of Claim 1, further comprising a database in which included are: proportional constants that are each a ratio of a number of particles relative to a beam quantity, with respect to the particle beam; z-direction dose distributions that are each a dose distribution in a traveling direction of the particle beam; x-direction dose distributions that are each a dose distribution in an x-direction perpendicular to the traveling direction of the particle beam; and y-direction dose distributions that are each a dose distribution in a y-direction perpendicular to the traveling direction of the particle beam and the x-direction;

wherein the total dose calculator calculates the radiated number of particles by multiplying a selected proportional constant selected from among the proportional constants correspondingly to the measured energy, by the measured beam quantity, and wherein, at the time the unit particle dose is calculated, the total dose calculator calculates the unit particle dose by multiplying:
a selected z-direction dose selected from the z-direction dose distributions correspondingly to the measured energy;
a selected x-direction dose selected from the x-direction dose distributions correspondingly to a position in the x-direction with respect to the measured position of beam central axis, and to the measured energy; and
a selected y-direction dose selected from the y-direction dose distributions correspondingly to a position in the y-direction with respect to the measured position of beam central axis, and to the measured energy.

11. The dose distribution calculation device of claim 10, wherein the database stores therein, x-direction kick angles that are each a deflection angle given by the scanning device in the x-direction of the particle beam, and y-direction kick angles that are each a deflection angle given by the scanning device in the y-direction of the particle beam; and wherein, the total dose calculator calculates: at the time the selected x-direction dose is selected, an x-coordinate on the basis of a selected x-direction kick angle that is selected from among the x-direction kick angles correspondingly to the position in the x-direction with respect to the measured position of beam central axis, and to the measured energy, and then selects from the x-direction dose distributions, a dose corresponding to the x-coordinate as the selected x-direction dose;

and calculates, at the time the selected y-direction dose is selected, a y-coordinate on the basis of a selected y-direction kick angle that is selected from among the y-direction kick angles correspondingly to the position in the y-direction with respect to the measured position of beam central axis, and to the measured energy, and then selects from the y-direction dose distributions, a dose corresponding to the y-coordinate as the selected y-direction dose.

12. A particle beam therapy system comprising:
a particle beam generation apparatus for generating a particle beam with energy required for a particle beam therapy; a scanning device for deflecting the particle beam in two direction perpendicular to its beam traveling direction, to thereby scan the particle beam at a place where an irradiation target is placed; a beam transport apparatus for transporting the particle beam to the scanning device; a beam energy measuring device for measuring the energy of the particle beam generated by the particle beam generation apparatus; a beam-central axis measuring device for measuring a position of beam central axis through calculation based on an intensity of a magnetic field induced on a pathway of the particle beam by the scanning device; a beam quantity measuring device for measuring a beam quantity of the particle beam generated by the particle beam generation apparatus; and a dose distribution calculation device for calculating a radiation dose distribution to be applied by the particle beam to the irradiation target;
wherein said dose distribution calculation device is the dose distribution calculation device of claim 1.

13. A dose distribution calculation method of calculating, when a particle beam therapy system performs a particle beam therapy by scanning using a scanning device a particle beam on a treatment target, a radiation dose distribution to be applied by the particle beam therapy system to the treatment target, said dose distribution calculation method comprising:

a confirmative radiation step of radiating the particle beam to a phantom as a substitute for the treatment target;

a data measuring step of measuring an energy, a beam quantity and a position of beam central axis, that are particle beam information of the particle beam generated by the particle beam therapy system, at multiple time points during the confirmative radiation step, to thereby collect respective measured energies, respective measured beam quantities and respective measured positions of beam central axis; and a total dose-distribution calculation step of calculating the radiation dose distribution on the basis of the measured energy, the measured beam quantity and the measured position of beam central axis in each of time segments in which the particle beam information is measured;

wherein, in the total dose-distribution calculation step, a dose at a calculation target point in the treatment target is calculated by adding together every time-segmental dose therefor, over all of the time segments, said every time-segmental dose resulting from multiplying a radiated number of particles calculated based on the measured energy and the measured beam quantity in a common segment in the time segments, by a unit particle dose that is a dose to be imparted by one particle in the particle beam and that is calculated based on the measured energy and the measured position of beam central axis in the common segment.

14. The dose distribution calculation device of claim 5, wherein the position of beam central axis is calculated based on an intensity of a magnetic field induced on a pathway of the particle beam by the scanning device.

15. The dose distribution calculation device of claim 2, wherein the particle beam information is measured at multiple time points during the confirmative radiation, so that the total dose calculator calculates a total dose distribution by adding together every dose distribution in each time segment.

16. The dose distribution calculation device of claim 3, wherein the particle beam information is measured at multiple time points during the confirmative radiation, so that the total dose calculator calculates a total dose distribution by adding together every dose distribution in each time segment.

17. The dose distribution calculation device of claim 4, wherein the particle beam information is measured at multiple time points during the confirmative radiation, so that the total dose calculator calculates a total dose distribution by adding together every dose distribution in each time segment.

18. The dose distribution calculation method of claim 13, further comprising:

comparing the radiation dose distribution calculated by the total dose calculator, with a planned dose distribution that is a dose distribution outputted by a treatment planning apparatus, to thereby issue an alarm when a difference between the radiation dose distribution and the planned dose distribution at their common calculation target point in the treatment target, is more than an allowability determination value.

19. The dose distribution calculation method of claim 13, further comprising:

comparing a dose value measured by a dosimeter placed in the phantom, with a calculated dose value in the radiation dose distribution calculated by the total dose calculator and corresponding to a placed position of the dosimeter, to thereby issue an alarm when a difference between these two dose values is more than an allowability determination value.

20. The dose distribution calculation method of claim 13, further comprising:

including in a database proportional constants that are each a ratio of a number of particles relative to a beam quantity, with respect to the particle beam; z-direction dose distributions that are each a dose distribution in a traveling direction of the particle beam; x-direction dose distributions that are each a dose distribution in an x-direction perpendicular to the traveling direction of the particle beam; and y-direction dose distributions that are each a dose distribution in a y-direction perpendicular to the traveling direction of the particle beam and the x-direction;

calculating the radiated number of particles by multiplying a selected proportional constant selected from among the proportional constants correspondingly to the measured energy, by the measured beam quantity; and at the time the unit particle dose is calculated, calculating the unit particle dose by multiplying:

a selected z-direction dose selected from the z-direction dose distributions correspondingly to the measured energy;

a selected x-direction dose selected from the x-direction dose distributions correspondingly to a position in the x-direction with respect to the measured position of beam central axis, and to the measured energy; and a selected y-direction dose selected from the y-direction dose distributions correspondingly to a position in the y-direction with respect to the measured position of beam central axis, and to the measured energy.

* * * * *